US012616541B2

(12) United States Patent
Tanimoto et al.

(10) Patent No.: US 12,616,541 B2
(45) Date of Patent: May 5, 2026

(54) SURGICAL ROBOT AND ROBOTIC SURGICAL SYSTEM

(71) Applicant: KAWASAKI JUKOGYO KABUSHIKI KAISHA, Kobe (JP)

(72) Inventors: Kenichirou Tanimoto, Kobe (JP); Fumiya Matsumoto, Kobe (JP); Tetsuya Nakanishi, Düsseldorf (DE)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 309 days.

(21) Appl. No.: 18/365,257

(22) Filed: Aug. 4, 2023

(65) Prior Publication Data

US 2024/0041548 A1 Feb. 8, 2024

(30) Foreign Application Priority Data

Aug. 5, 2022 (JP) ................................. 2022-125793

(51) Int. Cl.
| | |
|---|---|
| *A61B 34/37* | (2016.01) |
| *A61B 34/00* | (2016.01) |
| *A61B 34/30* | (2016.01) |

(52) U.S. Cl.
CPC .............. *A61B 34/37* (2016.02); *A61B 34/74* (2016.02); *A61B 2034/305* (2016.02)

(58) Field of Classification Search
CPC ......... A61B 34/37; A61B 34/30; A61B 34/74; A61B 2034/305; A61B 2034/742; A61B 2034/302

USPC .......................................................... 606/41
See application file for complete search history.

(56) References Cited

U.S. PATENT DOCUMENTS

| | | | |
|---|---|---|---|
| 2016/0089794 A1 | 3/2016 | Niu et al. | |
| 2018/0146932 A1 | 5/2018 | Suga | |
| 2020/0367979 A1 | 11/2020 | Laakso et al. | |
| 2020/0405375 A1* | 12/2020 | Shelton, IV ....... | A61B 18/1815 |
| 2022/0233255 A1 | 7/2022 | Kawabata et al. | |
| 2022/0294062 A1 | 9/2022 | Kamon et al. | |
| 2023/0080541 A1 | 3/2023 | Ishikawa | |

FOREIGN PATENT DOCUMENTS

| | | |
|---|---|---|
| JP | S63-62686 A | 3/1988 |
| JP | 6457994 B2 | 1/2019 |
| JP | 2020-151354 A | 9/2020 |
| JP | 6806406 B | 1/2021 |
| JP | 6806406 B1 | 1/2021 |
| JP | 2021-037571 A | 3/2021 |
| WO | 2021/112193 A1 | 6/2021 |

* cited by examiner

*Primary Examiner* — Beverly M Flanagan
(74) *Attorney, Agent, or Firm* — METROLEX IP LAW GROUP, PLLC; Robert L. Scott, Esq.

(57) ABSTRACT

A surgical robot according to this disclosure includes a wiring-line set that is arranged in a robot arm so that the wiring-line set extends in a longitudinal direction of the robot arm, and passes through a rotation axis of a first joint, which is configured to rotate in a bending direction of the robot arm, and through a plane orthogonal to the longitudinal direction of the robot arm.

18 Claims, 12 Drawing Sheets

100

ARM CONTROLLER

31a

POSITIONER CONTROLLER

31b

|      | 1ST SPEED REDUCER | GEAR PART | 2ND SPEED REDUCER | TOTAL REDUCTION RATIO |
|------|-------------------|-----------|-------------------|-----------------------|
| JT1  | r1 | r3a | r2 | r4a |
| JT2  | r1 | r3b | r2 | r4b |
| JT3  | r1 | r3c | r2 | r4c |
| JT4  | r1 | r3d | r2 | r4d |
| JT5  | r1 | r3e | r2 | r4e |
| JT6  | r1 | r3f | r2 | r4f |

200

201
201
201
201
201
201
201
201
201
201
201
201
201

SURGICAL ROBOT AND ROBOTIC SURGICAL SYSTEM

CROSS-REFERENCE TO RELATED APPLICATION

The priority application number JP2022-125793, a surgical robot, Aug. 5, 2022, Kenichirou TANIMOTO, Fumiya MATSUMOTO, and Tetsuya NAKANISHI, upon which this patent application is based, are hereby incorporated by reference.

BACKGROUND OF THE INVENTION

Field of the Invention

This disclosure relates to a surgical robot and a robotic surgical system.

Description of the Background Art

Conventionally, a surgical robot is known. For example, Japanese Laid-Open Patent Publication No. JP 2020-151354 discloses a medical manipulator including manipulator arms and a positioner configured to move the manipulator arm. In the Japanese Laid-Open Patent Publication No. JP 2020-151354, the positioner is a vertical multi-joint robot, and includes a plurality of links. The links are coupled to each other by joints configured to rotate in a direction in which the manipulator arm is bent. The joint includes an electric motor and a speed reducer. A power supply cable for supplying power to the positioner is held in the positioner. In the Japanese Laid-Open Patent Publication No. JP 2020-151354, a base end side part of the power supply cable extends in a direction different from a rotation axis direction of the speed reducer to bypass the speed reducer. Accordingly, size increase of the speed reducer can be prevented as compared with a configuration in which the power supply cable is inserted into an interior of a hollow shaft of the speed reducer whereby extending along a rotation axis of the speed reducer, and is then drawn to a lateral side of the speed reducer.

In the Japanese Laid-Open Patent Publication No. JP 2020-151354, the size increase of the speed reducer can be prevented by the arrangement in which the base end side part of the power supply cable extends in the direction different from the rotation axis direction of the speed reducer to bypass the speed reducer. Although this arrangement can prevent size increase of a manipulator arm, it is desired to a thinner manipulator arm.

SUMMARY OF THE INVENTION

The present disclosure is intended to solve the above problem, and provides a surgical robot and a robotic surgical system capable of thinning their robot arm.

In order to attain the aforementioned object, a surgical robot according to a first aspect of the present disclosure includes a robot arm including a fore end to which a surgical instrument is attached, and a joint; and a wiring-line set arranged in the robot arm, wherein the joint includes a first joint configured to rotate in a direction in which the robot arm is bent, and the wiring-line set is arranged in the robot arm so that the wiring-line set extends in a longitudinal direction of the robot arm, and passes through a rotation axis of the first joint and through a plane orthogonal to the longitudinal direction of the robot arm.

A surgical robot according to a second aspect of the present disclosure includes a robot arm including a free end to which a surgical instrument is attached, and first and second joints; and a wiring-line set arranged in the robot arm, wherein the first joint is configured to rotate in a direction in which the robot arm is bent, the second joint is configured to rotate about a longitudinal direction of the robot arm as a rotation axis, and the wiring-line set is arranged in the robot arm so that the wiring-line set extends in a longitudinal direction of the robot arm, and passes through a rotation axis of the first joint and through a plane orthogonal to the longitudinal direction of the robot arm, and extends along the rotation axis of the second joint.

A robotic surgical system according to a third aspect of the present disclosure includes a patient-side device including a robot arm that includes a fore end to which a surgical instrument is attached, and a joint(s); an operator-side device including an operation unit configured to accept an instruction from an operator; and a wiring-line set arranged in the robot arm, wherein the joint(s) includes/include a first joint configured to rotate in a direction in which the robot arm is bent, and the wiring-line set is arranged in the robot arm so that the wiring-line set extends in the longitudinal direction of the robot arm, and passes through a rotation axis of the first joint and through a plane orthogonal to the longitudinal direction of the robot arm.

In the surgical robots according to the first and second aspects of the present disclosure, and the robotic surgical system according to the third aspect of the present disclosure, as discussed above, the wiring-line set is arranged in the robot arm so that the wiring-line set extends in a longitudinal direction of the robot arm, and passes through a rotation axis of the first joint and through a plane orthogonal to the longitudinal direction of the robot arm. Consequently, because the wiring-line set will not bulge in the rotation axis direction of the first joint, a width (thickness) in the rotation axis direction of the robot arm is not necessarily increased. Therefore, the robot arm can be thinned.

According to the present disclosure, robot arm can be thinned.

DESCRIPTION OF THE PREFERRED EMBODIMENT (Configuration of Robotic Surgical System)

The following description describes a configuration of a robotic surgical system 100 according to this embodiment. The robotic surgical system 100 includes a surgical robot 1 and a remote control apparatus 2. The remote control apparatus 2 is an example of an operator-side device.

Figure 4:
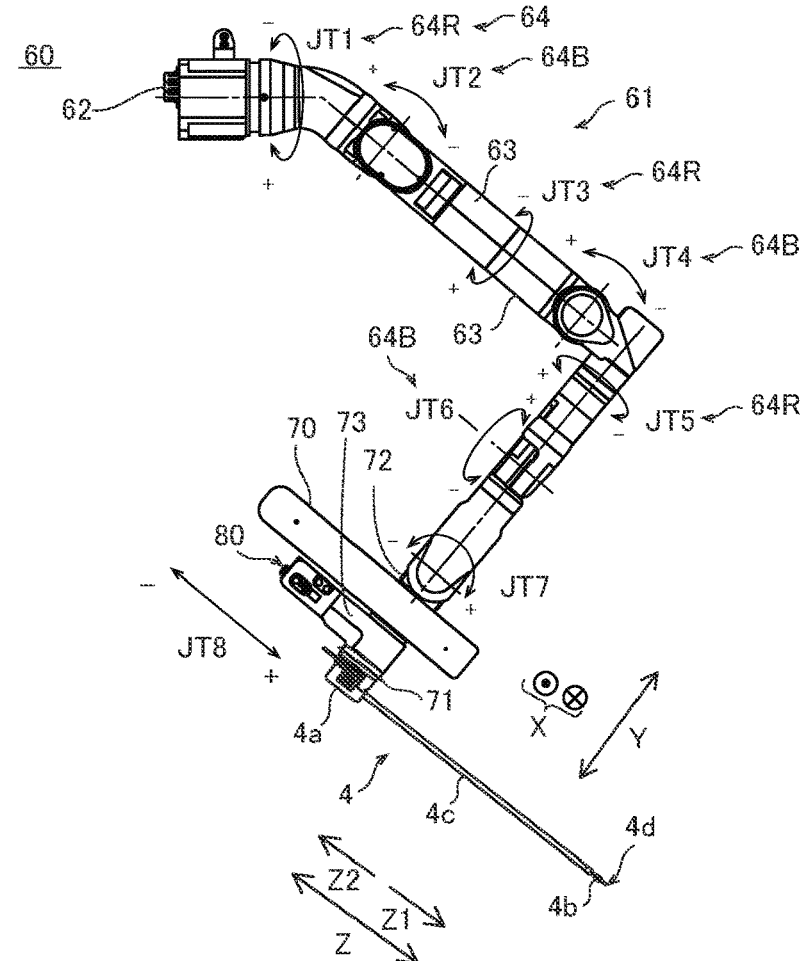
FIG. 4 is a block diagram showing a configuration of a robot arm according to the one embodiment.

In this specification, a longitudinal direction of a surgical instrument 4 is defined as a Z direction as shown in FIG. 4. A free-end side of the surgical instrument 4 is defined as a Z1 side, and a base-end side of the surgical instrument 4 is defined as a Z2 side. A direction orthogonal to the Z direction is defined as an X direction. A direction orthogonal to the Z direction and the X direction is defined as a Y direction.

Figure 3:
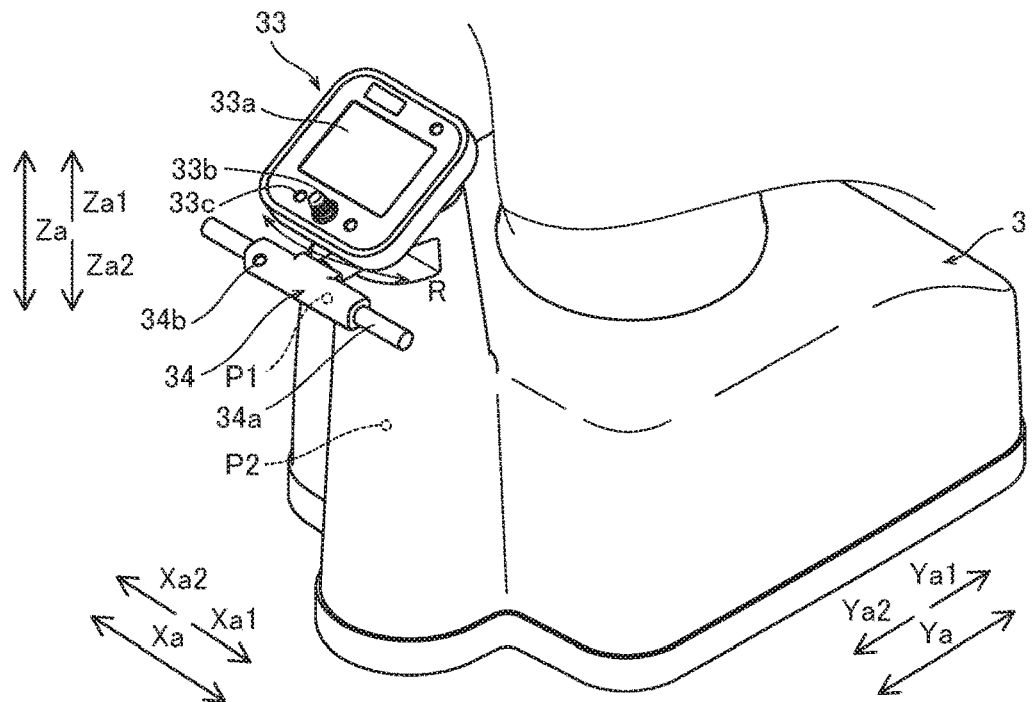
FIG. 3 is a diagram showing a configuration of the medical cart according to the one embodiment.

In this specification, a leftward/rightward direction from the viewpoint of an operator who operates a display 33a of an input device 33 is defined as an Xa direction as shown in FIG. 3. A rightward direction is defined as an Xa1 direction, and a leftward direction is defined as an Xa2 direction. A frontward/rearward direction from the viewpoint of the operator who operates the display 33a of the input device 33 is defined as a Ya direction. A frontward direction is defined as a Ya1 direction, and a rearward direction is defined as a Ya2 direction. A direction orthogonal to a floor on which the surgical robot 1 is arranged is defined as a Za direction. An upward direction is defined as a Za1 direction, and a downward direction is defined as a Za2 direction.

Figure 12:
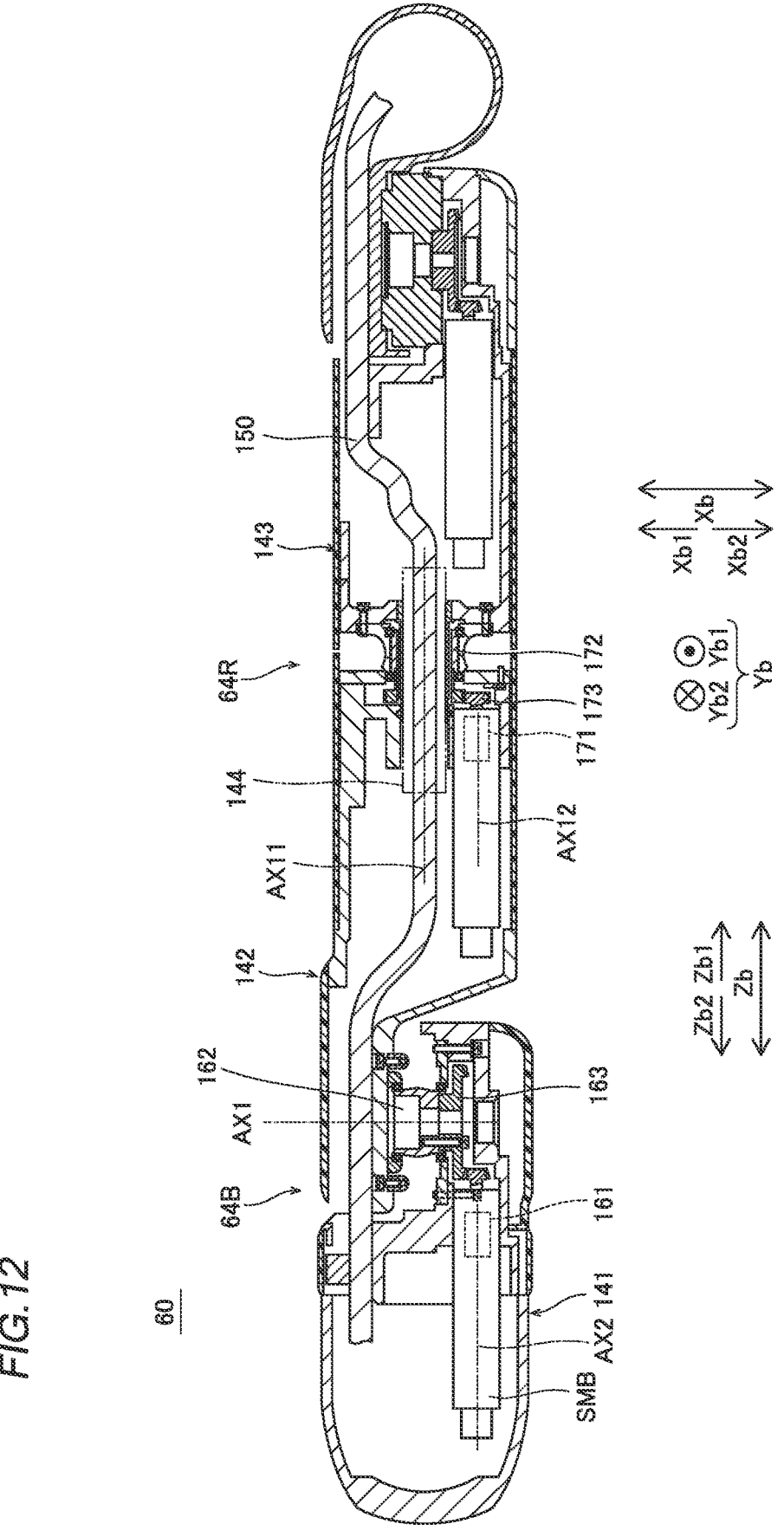
FIG. 12 is a cross-sectional diagram of the robot arm according to the one embodiment as viewed in a Yb direction.

In addition, this specification, as shown in FIG. 12, when a robot arm 60 does not bend, a longitudinal direction of a first housing 141, a second housing 142 and a third housing 143 discussed later is defined as a Zb direction. Also, a longitudinal direction of the robot arm 60 is defined as the Zb direction. As shown in FIG. 12, a direction orthogonal to the Zb direction and extending along a rotation axis AX1 of a joint 64B is defined as an Xb direction. A direction orthogonal to the Zb direction and the Xb direction is defined as a Yb direction.

Figure 1:
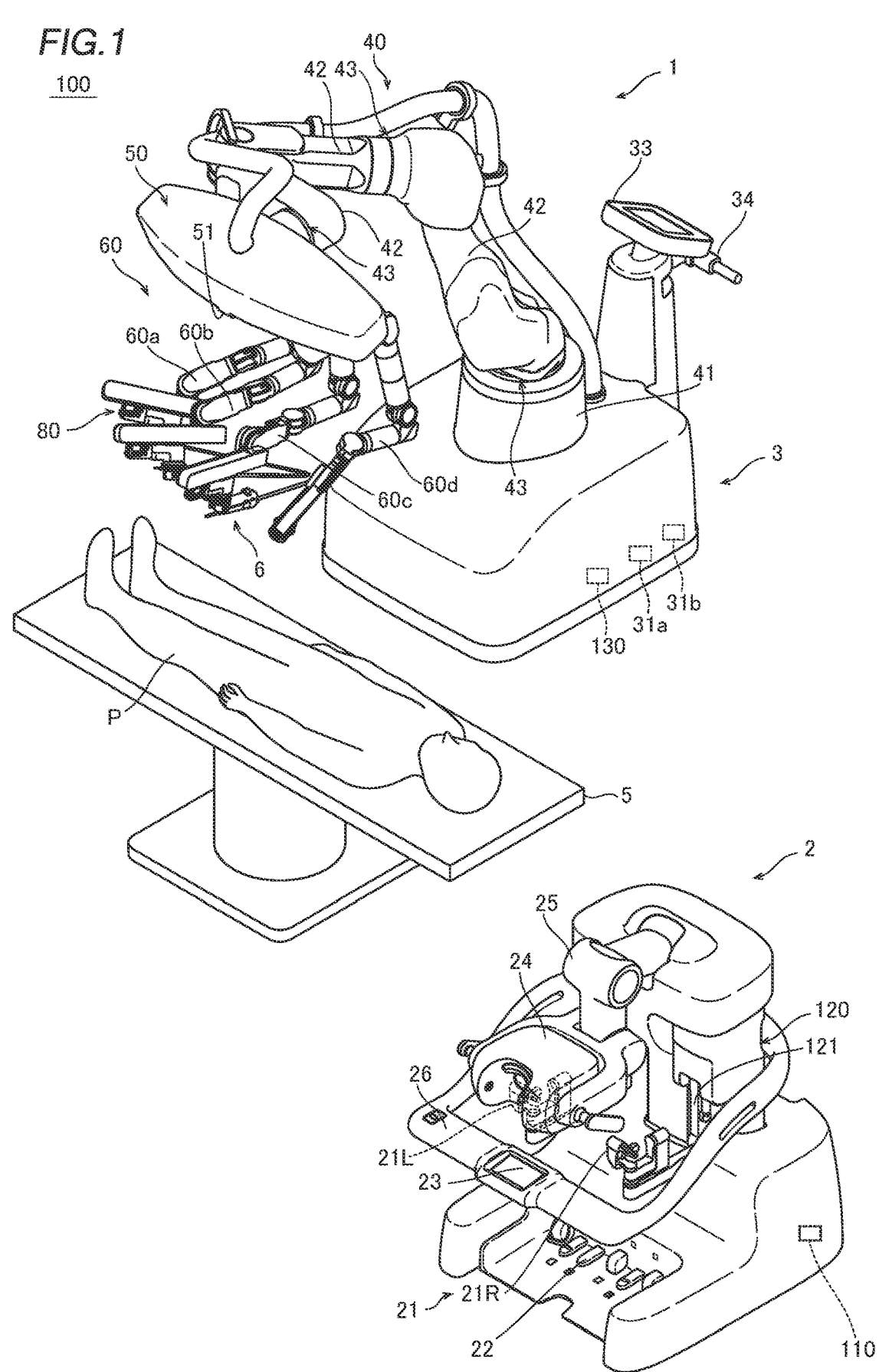
FIG. 1 is a block diagram showing a configuration of a robotic surgical system according to one embodiment.

As shown in FIG. 1, the surgical robot 1 is arranged in an operating room. A remote control apparatus 2 is located remote from the surgical robot 1. An operator, such as a doctor, can provide the remote control apparatus 2 with a command to direct a desired motion of the surgical assistance robot 1. The remote control apparatus 2 transmits the provided command to the surgical robot 1. The surgical robot 1 is configured to perform the motion in accordance with the command received. The surgical robot 1 is arranged in the operating room, which is a sterile field.

(Configuration of Surgical Robot)

As shown in FIG. 1, the surgical robot 1 includes a medical cart 3, a positioner 40, an arm base 50, a plurality of robot arms 60 and an arm operation unit 80.

As shown in FIG. 3, the medical cart 3 is configured to move the positioner 40. The medical cart 3 includes the input device 33. The input device 33 is configured to accept instructions to move or change orientations of the positioner 40, the arm base 50 and the plurality of robot arms 60 to prepare a surgical operation mainly before the operation is carried out. The medical cart 3 includes an operation handle 34, a stabilizer 34c and an electric cylinder 34d shown in FIG. 9.

Figure 2:
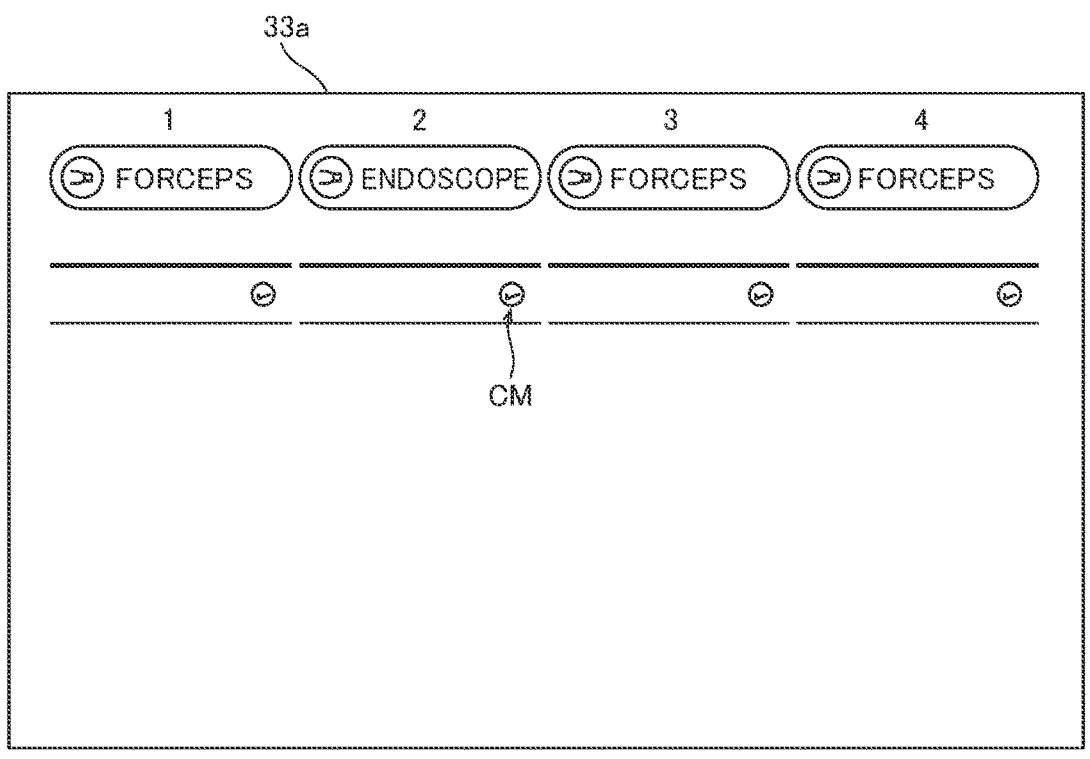
FIG. 2 is a diagram showing a display of a medical cart according to the one embodiment.

As shown in FIG. 2, the input device 33 includes a display 33a, a joystick 33b and an enable switch 33c. For example, the display 33a is a liquid crystal panel. The display 33a indicates numbers corresponding to the plurality of robot arms 60. Also, the display 33a indicates types of surgical instruments 4 attached to the plurality of robot arms 60. The display 33a indicates checkmarks CM representing that their pivot positions PP have been set.

As shown in FIG. 3, the joystick 33b is arranged in proximity to the input device 33 of the medical cart 3. When an operation mode displayed on the input device 33 is selected, the positioner 40 can be three-dimensionally moved by operating the joystick 33b.

The enable switch 33c is arranged in proximity to the joystick 33b of the medical cart 3. The enable switch 33c is configured to enable or disable movement of the positioner 40. When the enable switch 33c is pressed so that movement of the positioner 40 is enabled, the positioner 40 can be moved in accordance with a manual operation of the joystick 33b.

Also, the operation handle 34 is arranged in proximity to the display 33a of the medical cart 3. The operating handle 34 includes a throttle grip 34a that is configured to be gripped and twisted by an operator such as nurse, engineer, etc. to control movement of the medical cart 3. Specifically, the operation handle 34 is arranged under the input device 33. The medical cart 3 can move forward when the throttle grip 34a is twisted from a near side toward a far side. The medical cart 3 can move backward when the throttle grip 34a is twisted from the far side toward the near side. A speed of the medical cart 3 can be changed in accordance with a twisting amount of the throttle grip 34a. In addition, the operation handle 34 is configured to swing leftward and rightward as shown by an R direction, and to rotate the medical cart 3 depending on the swinging operation of the operation handle 34.

Also, the operation handle 34 of the medical cart 3 includes an enable switch 34b configured to enable or disable movement of the medical cart 3. When the enable switch 34b is pressed so that movement of the medical cart 3 is enabled, the medical cart 3 can be moved in accordance with a manual operation of the throttle grip 34a of the operating handle 34.

For example, as shown in FIG. 1, the positioner 40 is constructed of a 7-axis multi-joint robot. The positioner 40 is arranged on the medical cart 3. The positioner 40 is configured to adjust a position of the arm base 50. The positioner 40 can move the position of the arm base 50 in three dimensions.

The positioner 40 includes a base 41, and a plurality of links 42 coupled to the base 41. The links 42 are coupled to each other by joints 43.

The arm base 50 is attached to a free end of the positioner 40. The base ends of the plurality of robot arms 60 are attached to the arm base 50. The plurality of robot arms 60 are foldable into a storage posture. The arm base 50 and the plurality of robot arms 60 covered by sterile drapes when used. The robot arm 60 is configured to support surgical instruments 4.

Figure 9:
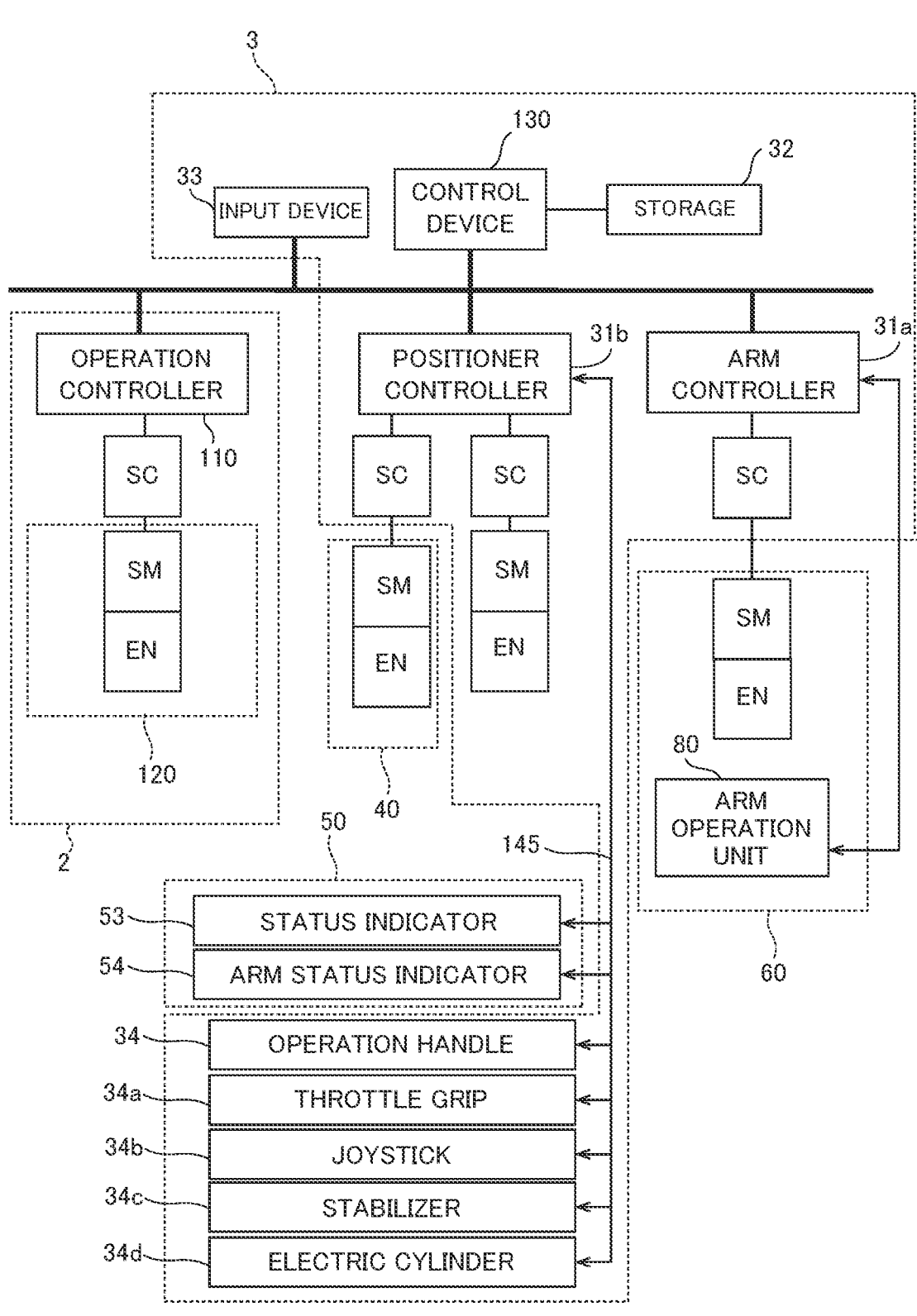
FIG. 9 is a control block diagram of a surgical robot according to the one embodiment.

A status indicator 53 and an arm status indicator 54 shown in FIG. 9 are provided in the arm base 50. The status indicator 53 is configured to indicate a status of robotic surgical system 100. The arm status indicator 54 is configured to indicate states of robot arms 60.

Two or more robot arms 60 are provided as plurality of robot arms 60. Specifically, four robot arms 60*a*, 60*b*, 60*c* and 60*d* are provided. The robot arms 60*a*, 60*b*, 60*c* and 60*d* have a similar configuration to each other.

As shown in FIG. 4, each robot arm 60 includes an arm 61, a first link part 72, a second link part 73, a translation mechanism 70, and a joint 64.

The robot arm 60 has JT1, JT2, JT3, JT4, JT5, JT6 and JT7 axes as rotation axes, and a JT8 axis as a linear-motion axis. The axes from JT1 to JT7 are rotation axes of the joint 64 of the arm 61. The JT7 axis is a rotational axis of the first link part 72. The JT8 axis is a linear-motion axis along which the second link part 73 is moved relative to the first link part 72 in the Z direction by the translation mechanism 70. The arm 61 includes a base 62, links 63 and joints 64.

In this embodiment, the joints 64 include joints 64B and joints 64R. The joint 64B is a bending (hinge) joint configured to rotate so that the robot arm 60 can be folded. A rotation axis of joint 64B is referred to as a bend axis. The joints 64 that have the JT2 axis, the JT4 axis, and the JT6 axis as rotation axes are the joints 64B. The joint 64R is a bending joint that rotates about a longitudinal direction of the robot arm 60 as a rotation axis. The rotation axis of the joint 64R is referred to as a roll axis. The joint 64 that has the JT1 axis, the JT3 axis, and the JT5 axis as rotation axes is the joint 64R, which is a twisting joint. Structures of the joint 64B and the joint 64R will be described in detail later. The joints 64B and 64R are examples of first and second joints, respectively.

The arm 61 is constructed of a 7-axis multi-joint robot arm. The first link part 72 is arranged in a free end of arm 61. The arm operation unit 80 discussed later is attached to the second link part 73. The translation mechanism 70 is arranged between the first link part 72 and the second link part 73. The second link part 73 includes a holder 71 configured to hold the surgical instrument 4.

Surgical instruments 4 can be attached to the free ends of the plurality of robot arms 60. The surgical instruments 4 include, for example, replaceable instruments, an endoscope 6 configured to capture images of a part to be operated, a pivot-position setting tool 7 to set a pivot position PP described below, etc. The surgical instrument 4 as the instrument includes a driven unit 4*a*, a forceps 4*b* and a shaft 4*c*.

As shown in FIG. 1, an endoscope 6 is attached to the free end of one, e.g., the robot arm 60*c* of the robot arms 60, and the surgical instruments 4 other than the endoscope 6 are attached to the free ends of the robot arms 60*a*, 60*b* and 60*d*. The endoscope 6 is attached to one of two robot arms 60*b* and 60*c*, which are located in a central part, of the four robot arms 60 arranged adjacent to each other.

(Configuration of Instrument)

Figure 5:
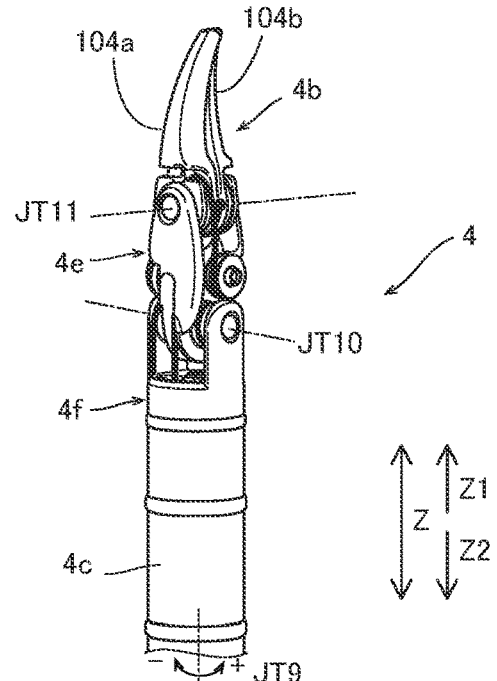
FIG. 5 is a diagram showing a forceps.

For example, as shown in FIG. 5, a forceps 4*b* is attached to the free end of the instrument. Tools that include a joint and can be attached to the free end of the instrument can include scissors, a grasper, a needle holder, a microdissector, a staple applier, a tucker, a vacuum cleaning tool, a snare wire, a clip applier, etc., other than the forceps 4*b*. Tools that do not include any joint and can be attached to the free end of the instrument can include a cutting blade, a cautery probe, a cleaner, a catheter, a vacuum orifice, etc.

Forceps 4*b* includes a first support 4*e* and a second support 4*f*. The first support 4*e* is configured to rotatably support a base end side of jaws 104*a* and 104*b* about a JT11 axis. The second support 4*f* is rotatably configured to support a base-end side of the first support 4*e* about a JT10 axis. The shaft 4*c* can rotate about a JT9 axis. The jaws 104*a* and 104*b* can pivot about the JT11 axis to open and close.

(Configuration of Arm Operation Unit)

Figure 6:
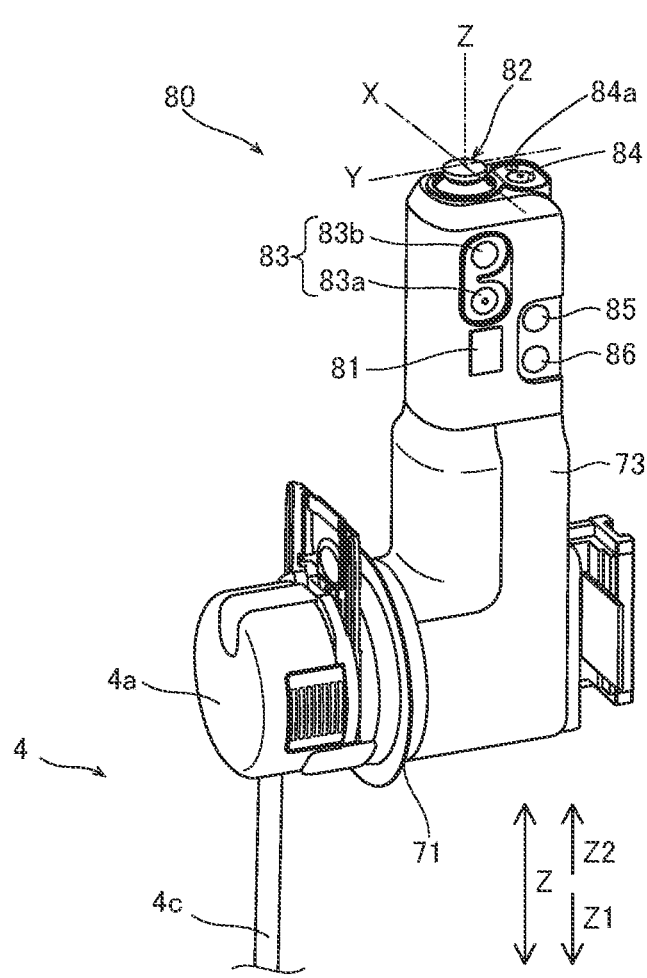
FIG. 6 is a block diagram showing a configuration of an arm operation unit according to the one embodiment.

As shown in FIG. 6, the arm control unit 80 is mounted to the robot arm 60, and is configured to operate the robot arm 60. Specifically, the arm operation unit 80 is mounted to the second link part 73.

The arm control unit 80 includes an enable switch 81, a joystick 82, linear switches 83, a mode switching button 84, a mode indicator 84*a*, a pivot button 85, and an adjustment button 86.

The enable switch 81 is configured to enable or disable movement of the robot arm 60 by means of the joystick 82 and the linear switches 83. Movement of the surgical instrument 4 by the robot arm 60 is enabled when the enable switch 81 is pressed while the arm operation unit 80 is grasped by an operator such as nurse, assistant, etc.

The joystick 82 is an operation tool configured to control movement of the surgical instrument 4 by the robot arm 60. The joystick 82 is an operation tool configured to control a moving direction and a moving speed of the robot arm 60. The robot arm 60 can be moved in accordance with to a tilting direction and a tilting angle of the joystick 82.

The linear switches 83 are a switch for moving the surgical instrument 4 in the Z direction, which is a longitudinal direction of the instrument 4. The linear switches 83 includes a linear switch 83*a* for moving the surgical instrument 4 in a direction in which the surgical instrument 4 is inserted into a patient P, and a linear switch 83*b* for moving the surgical instrument 4 in a direction in which the surgical instrument 4 is moved away from the patient P. The linear switch 83*a* and the linear switch 83*b* are constructed of a press-button switch.

Figure 7:
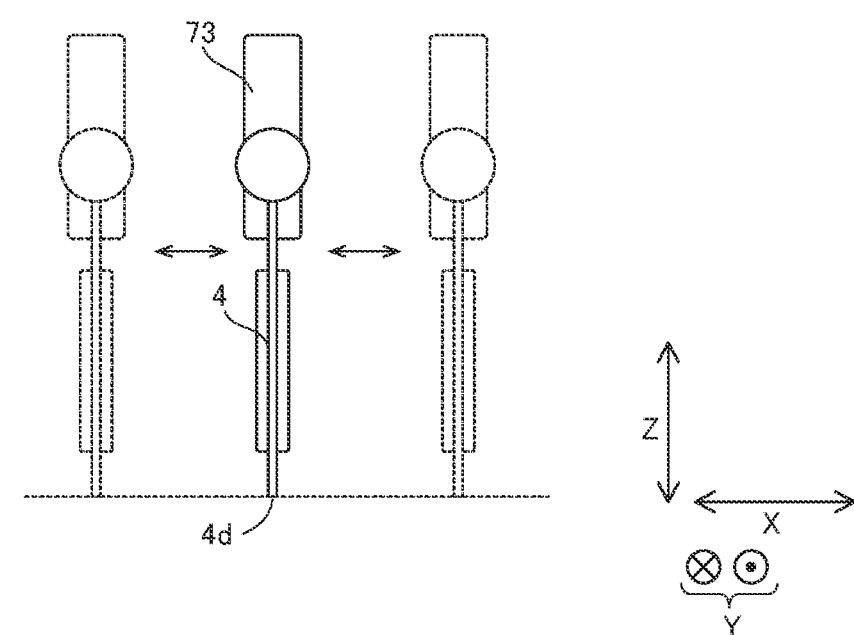
FIG. 7 is a diagram illustrating translational movement of the robot arm.
Figure 8:
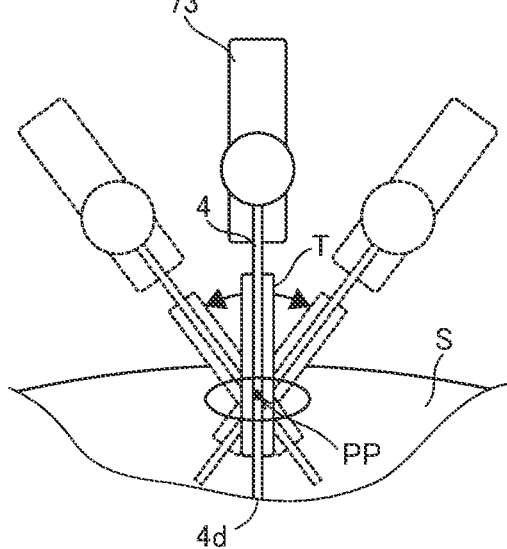
FIG. 8 is a diagram illustrating rotational movement of the robot arm.

The mode switching button 84 is a press-button switch for switching between a translation mode in which the surgical instrument 4 is translationally moved as shown in FIG. 7, and a rotation mode in which the surgical instrument 4 is rotated as shown in FIG. 8. As shown in FIG. 7, in the translation mode in which the robot arm 60 is translationally moved, the robot arm 60 can be moved so that the free end 4*d* of the surgical instrument 4 can be moved in an X-Y plane. As shown in FIG. 8, in the rotation mode in which the robot arm 60 is rotated, in a case in which any pivot position PP is not stored in the storage 32, the robot arm 60 can be moved so that the forceps 4*b* can be rotated about a center of the forceps 4*b*, and in a case in which a pivot position PP is stored in the storage 32, the robot arm 60 can be moved so that the forceps 4*b* can be rotated about a center of the forceps 4*b* on the JT11 axis. In this case, the surgical instrument 4 is rotated with the shaft 4*c* of the surgical instrument 4 being inserted into a trocar T. The mode switching button 84 is arranged on a surface on a Z-direction side of the arm operation unit 80.

The mode indicator 84*a* is configured to indicate which mode is selected. The mode indicator 84*a* is configured to light on to indicate the rotation mode, and to light off indicate the translation mode. The mode indicator 84a also serves as a pivot position indicator to indicate that the pivot position PP is set. The mode indicator 84a is arranged on the surface on the Z-direction side of the arm operation unit 80.

The pivot button 85 is a press-button switch configured to set the pivot position PP, which corresponds to the rotation axis of the surgical instrument 4 attached to the robot arm 60.

The adjustment button 86 is a button configured to optimize a position of the robot arm 60. After the pivot position PP is set with respect to the robot arm 60 to which the endoscope 6 is attached, when the adjustment button 86 is pressed positions of the other robot arms 60 and the arm base 50 is optimized.

(Remote Control Apparatus)

For example, as shown in FIG. 1, the remote control apparatus 2 is arranged in an operating room or outside the operating room. The remote control apparatus 2 includes operation units 120 including an arm 121 and an operation handle 21, a foot pedal 22, a touch panel 23, a monitor 24, a support arm 25, and a support bar 26. The operation units 120 serve as a handle for operation that is configured to receive commands from an operator such as doctor.

The operation units 120 are a handle configured to manipulate the surgical instrument 4. Also, the operation units 120 are configured to receive manipulated amounts corresponding to the surgical instruments 4. A control device 130 discussed later is configured to control the surgical instrument 4 and the robot arm 60 so that the surgical instruments 4 are moved to desired positions in accordance with the manipulated amounts of the operation unit 120. The operation units 120 include an operation unit 120 that is arranged on a left side from viewpoint of an operator such as doctor and is configured to be manually operated by operator's left hand, and an operation unit 120 that is arranged on a right side from viewpoint of the operator such as doctor and is configured to be manually operated by operator's right hand. The operation unit 120L and the operation unit 120R include an operation handle 21L and an operation handle 21R, respectively.

The monitor 24 is a scope-type display device configured to display images captured by the endoscope 6. The support arm 25 supports the monitor 24, and can adjust a height of the monitor 24 to a height of eyes of the operator such as doctor. The touch panel 23 is arranged on the support bar 26. When a head of the operator is detected by a sensor arranged in proximity to the monitor 24, the surgical robot 1 can accept manual operations from the remote control apparatus 2. The operator will manually operate the operation unit 120 and the foot pedal 22 while seeing of an affected area on the monitor 24. Commands can be provided to the remote control apparatus 2 in accordance with these manual operations. Instructions provided to the remote control apparatus 2 are transmitted to the surgical assistance robot 1.

(Configuration of Control System)

As shown in FIG. 9, robotic surgical system 100 includes a control device 130, an arm controller 31a, a positioner controller 31b, and an operation controller 110.

The control device 130 is accommodated in the medical cart 3, and configured to communicate with the arm controller 31a and the positioner controller 31b so that the robotic surgical system 100 is entirely controlled. Specifically, the control device 130 is configured to control the arm controller 31a, the positioner controller 31b and the operation controller 110 by using the communications with them. The control device 130 is connected to the arm controller

31a, the positioner controller 31b and the operation controller 110 through LAN, etc. The control unit 130 is arranged in the medical cart 3.

Each of the plurality of robot arms 60 includes the arm controller 31a. In other words, a plurality of arm controllers 31a the number of which corresponds to the number of the plurality of robot arms 60 are included in the medical cart 3.

As shown in FIG. 9, the input device 33 is connected to the control device 130 through LAN, etc. The status indicator 53, the arm status indicator 54, the operation handle 34, the throttle grip 34a, the joystick 33b, the stabilizer 34c and the electric cylinder 34d are connected to the positioner controller 31b through a wire line 145 by means of a communication network that can share information with them by using serial communication. Although all of the status indicator 53, arm status indicator 54, and the like are connected to each other through one wiring line 145 in FIG. 9, wiring lines 145 are actually provided to each of the status indicator 53, the arm status indicator 54, the operation handle 34, the throttle grip 34a, the joystick 33b, the stabilizer 34c and the electric cylinder 34d.

Figure 10:
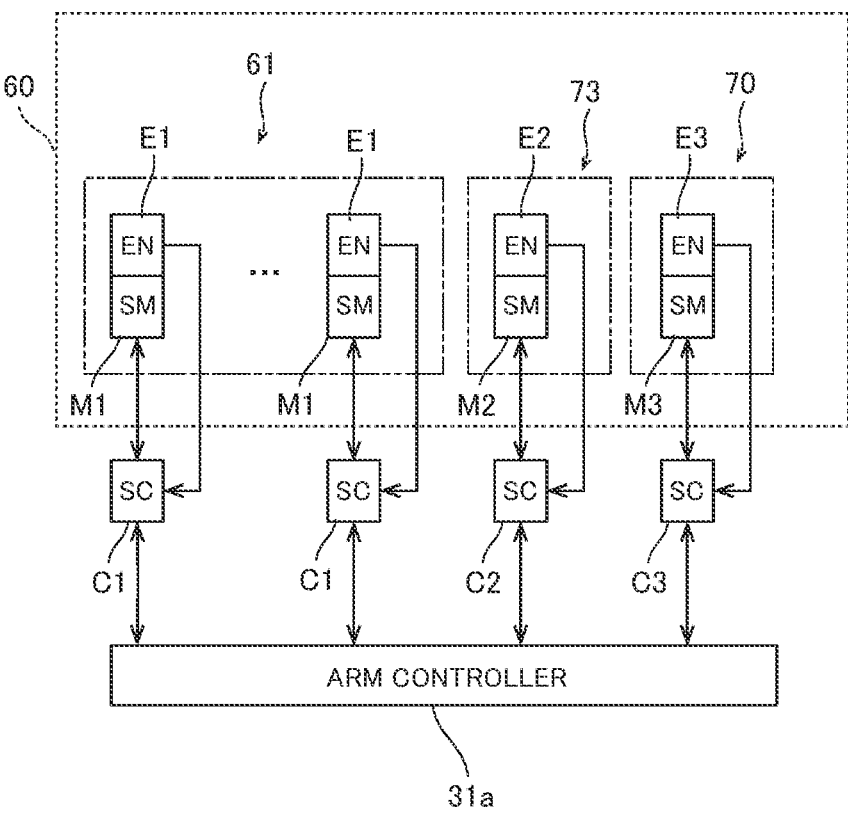
FIG. 10 is a control block diagram of the robot arm according to the one embodiment.

As shown in FIG. 10, each arm 61 includes a plurality of servomotors M1, a plurality of encoders E1 and a plurality of speed reducers corresponding to a plurality of joints 64. The encoder E1 is configured to detect a rotation angle of the servomotor M1. The speed reducer is configured to reduce a rotation of the servomotor M1 whereby increasing its torque. A servo controller C1 is configured to control the servomotor M1, and is arranged in the medical cart 3 adjacent to the arm controller 31a. Also, the encoder E1 is configured to detect the rotation angle of the servomotor M1, and is electrically connected to the servo controller C1.

The second link part 73 includes a servomotor M2 configured to rotate a driven member arranged in a driven unit 4a of the surgical instrument 4, an encoder E2, and a speed reducer. The encoder E2 is configured to detect a rotation angle of the servomotor M2. The speed reducer is configured to reduce a rotation of the servomotor M2 whereby increasing its torque. The medical cart 3 includes a servo controller C2 configured to control the servomotor M2 for driving the surgical instrument 4. The encoder E2 for detecting the rotation angle of the servo motor M2 is electrically connected to the servo control unit C2. Note that a plurality of servomotors M2, a plurality of encoders E2 and a plurality of servo controllers C2 are included.

The translation mechanism 70 includes a servomotor M3 configured to translationally move the surgical instrument 4, an encoder E3, and a speed reducer. The encoder E3 is configured to detect a rotation angle of the servomotor M3. The speed reducer is configured to reduce a rotation of the servomotor M3 whereby increasing its torque. The medical cart 3 includes a servo controller C3 configured to control the servomotor M3 for translationally moving the surgical instrument 4. The encoder E3 for detecting the rotation angle of the servo motor M3 is electrically connected to the servo control unit C3.

Figure 11:
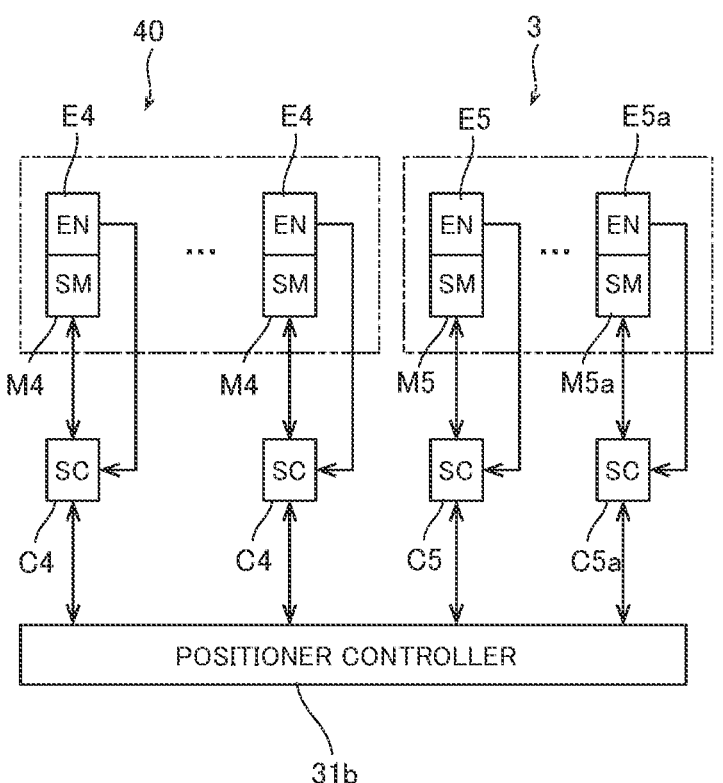
FIG. 11 is a control block diagram of the medical cart and a positioner according to the one embodiment.

As shown in FIG. 11, the positioner 40 includes a plurality of servomotors M4, a plurality of encoders E4 and a plurality of speed reducers corresponding to a plurality of joints 43 of the positioner 40. Each encoder E4 is configured to detect a rotation angle of the servomotor M4. The speed reducer is configured to reduce a rotation of the servomotor M4 whereby increasing its torque.

The medical cart 3 includes front wheels as driving wheels, and rear wheels configured to be steered by manually operating the handle 34. The rear wheels are arranged closer to the operating handle 34 with respect to the front wheels. The medical cart 3 includes a servomotor M5 configured to drive the front wheels of the medical cart 3, an encoder E5, speed reducers, and brakes. The speed reducer is configured to reduce a rotation of the servomotor M5 whereby increasing its torque. Also, the operation handle 34 of the medical cart 3 includes a potentiometer P1 shown in FIG. 3, and the servomotor M5 of the front wheels can be driven in accordance with a rotation angle detected by the potentiometer P1 in response to a twisting amount of the throttle grip 34a. The rear wheels of the medical cart 3 have a twin-wheel type structure, and the rear wheels can be steered in accordance with a rightward/leftward turn of the operating handle 34. Also, the operation handle 34 of the medical cart 3 includes a potentiometer P2 shown in FIG. 3 on a turning shaft, and the rear wheel of medical cart 3 is provided with a servomotor M5a, an encoder E5a, and speed reducers. The speed reducer is configured to reduce a rotation of the servomotor M5a whereby increasing its torque. The servomotor M5a can be driven in accordance with a rotation angle detected by the potentiometer P2 in response to a rightward/leftward turning amount of the operation handle 34. In other words, power is assisted by the servomotor M5a when the rear wheels are steered by turning the operation handle 34 rightward or leftward.

The medical cart 3 can be moved forward or rearward by driving the front wheels. Also, the medical cart 3 can be turned rightward or leftward by steering the rear wheels by turning the operating handle 34 of the medical cart 3.

As shown in FIG. 11, the medical cart 3 includes servo controllers C4 configured to control the servomotors M4 for moving the positioner 40. Also, the encoder E4 is configured to detect the rotation angle of the servomotor M4, and is electrically connected to the servo controller C4. The medical cart 3 includes a servo controller C5 configured to control the servomotor M5 for driving the front wheels of the medical cart 3. The encoder E5 for detecting the rotation angle of the servo motor M5 is electrically connected to the servo control unit C5. The medical cart 3 includes a servo controller C5a configured to control the servomotor M5a for power assistance to steering of the rear wheels of the medical cart 3. The encoder E5a for detecting the rotation angle of the servo motor M5a is electrically connected to the servo control unit C5a.

As shown in FIG. 9, the control device 130 is configured to control the robot arm 60 in accordance with manual operations received by the arm operation unit 80. For example, the control device 130 is configured to control the robot arm 60 in accordance with manual operations received by the joystick 82 of the arm control unit 80. Specifically, the arm controller 31a provides an input signal provided from the joystick 82 to the control device 130. The control device 130 generates position commands based on the received input signal and the rotation angles detected by the encoders E1, and provides the position commands to the servo controllers C1 via the arm controller 31a. The servo controllers C1 generate current commands based on the position commands provided from the arm controller 31a and the rotation angles detected by the encoders E1, and provide the current commands to the servomotors M1. Accordingly, the robot arm 60 is moved in accordance with an operation command provided to the joystick 82.

The control device 130 controls the robot arm 60 based on an input signal from the linear switch 83 of the arm operation unit 80. Specifically, the arm controller 31a provides an input signal provided from the linear switch 83 to the control device 130. The control device 130 generates position commands based on the received input signal and the rotation angles detected by the encoder E1 or E3, and provides the position commands to the servo controller C1 or C3 via the arm controller 31a. The servo controller C1 or C3 generate current commands based on the position commands provided from the arm controller 31a and the rotation angles detected by the encoder E1 or E3, and provide the current commands to the servomotor M1 or M3. Accordingly, the robot arm 60 is moved in accordance with an operation command provided to the linear switch 83.

The medical cart 3 includes the positioner controller 31b. The positioner controller 31b is configured to control the positioner 40 and the medical cart 3. The positioner 40 includes a plurality of servomotors SM, a plurality of encoders EN and a plurality of speed reducers corresponding to a plurality of joints 43 of the positioner 40. The medical cart 3 includes the servo controllers SC configured to control the servomotors SM of the positioner 40. The medical cart 3 includes servomotors SM configured to drive the front wheels of the medical cart 3, the encoders EN, speed reducers, the servo controllers SC, and brakes.

The operation controller 110 is provided in a main body of the remote control apparatus 2. The operation controller 110 is configured to control the operation units 120. The operation controller 110 is associated with both the left-hand side operation unit 120 and the right-hand side operation unit 120. The operation unit 120 includes servomotors SM, encoders EN and speed reducers corresponding to the plurality of joints of the operation unit 120. The servo controllers SC configured to control the servomotors SM of the operation unit 120 is provided in the main body of the remote control apparatus 2 adjacent to the operation controller 110.

(Detailed Structure of Robot Arm)

As shown in FIG. 12, the robot arm 60 includes a first housing 141, a second housing 142 and a third housing 143. The robot arm 60 includes wiring 150. The first housing 141 and the second housing 142 are configured to rotate with respect to each other by means of the joint 64B as the bend axis. The second housing 142 and the third housing 143 are configured to rotate with respect to each other by means of the joint 64R as the roll axis. The first housing 141, the second housing 142 and the third housing 143 have a cylindrical shape. In other words, the first housing 141, the second housing 142 and the third housing 143 are hollow. The first housing 141, the second housing 142 and the third housing 143 are formed of metal, for example.

Figures 13, 14:
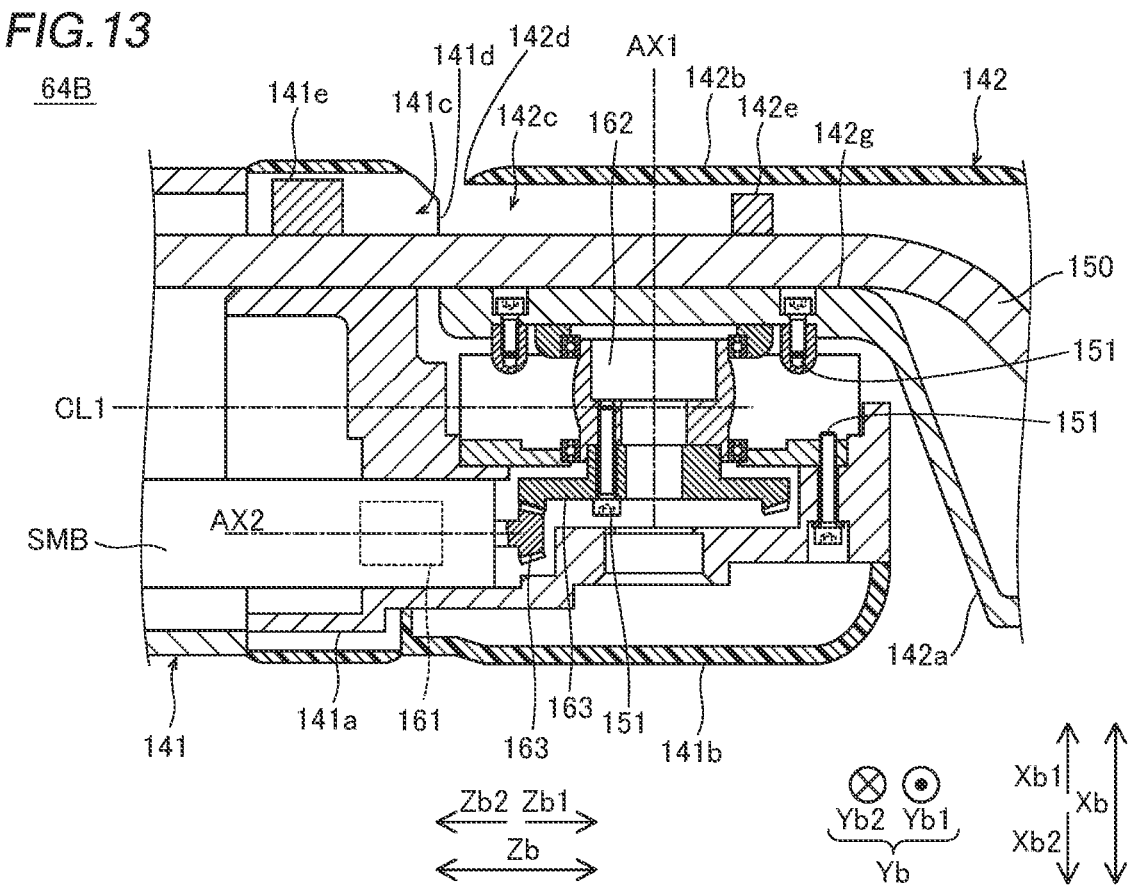
FIG. 13 is a cross-sectional diagram of a bending joint according to the one embodiment as viewed in the Yb direction.
FIG. 14 is a diagram showing speed reduction ratios of joints.

As shown in FIG. 13, the first housing 141 includes a frame part 141a formed of metal, and a cover part 141b formed of resin. A free end side of the first housing 141, which is a part on a Zb1 side of the first housing 141, has a stepped shape. The second housing 142 includes a frame part 142a formed of metal, and a cover part 142b formed of resin. A free end side of the second housing 142, which is a part on a Zb2 side of the second housing 142, has a stepped shape.

(Detailed Structure of Bending Joint Corresponding to Bend Axis)

The detailed structure of the joint 64B as a bending joint is now described. In this embodiment, as shown in FIG. 13, the joint 64B includes a servomotor SMB, a first speed reducer 161, bevel gears 163 and a second speed reducer 162. The servomotor SMB is an example of a first electric motor. The second speed reducer 162 is an example of a first-joint speed reducer.

The servomotor SMB is a relatively small electric motor. For example, the maximum diameter of the servomotor SMB is approximately 35 mm. Also, the servomotor SMB is a high-speed type electric motor. For example, the servomotor SMB can rotate at a speed of not smaller than 7500 rpm. The speed of the servomotor SMB is 10000 rpm, for example. The servomotor SMB is mounted to the frame part 141*a* of the first housing 141.

In this embodiment, the first speed reducer 161 is configured to reduce a speed of rotation of the servomotor SMB, and to provide the speed-reduced rotation. The first speed reducer 161 includes a planetary speed reducer. The planetary speed reducer includes a planetary gear train. The planetary gear train is a gear assembly including a sun gear having a center axis, and a plurality of planetary gears configured to rotate about their axis while rolling around the sun gear.

In this embodiment, the servomotor SMB and the first speed reducer 161 are integrally formed. A rotation axis AX2 of the servomotor SMB agrees with a rotation axis AX2 of the first speed reducer 161. The servomotor SMB and the first speed reducer 161 are arranged from a Zb2 side to the Zb1 side in this order.

In this embodiment, the bevel gears 163 are configured to further reduce the speed of the rotation provided from the first speed reducer 161, and to provide the further-speed-reduced rotation. The bevel gears 163 are configured to transmit the rotation of the servomotor SMB in a direction orthogonal to the rotation axis AX2 of the servomotor SMB. That is, the rotation axis AX1 of one of the bevel gears 163 is orthogonal to the rotation axis AX2 of the servomotor SMB. The bevel gears 163 are an umbrella gear having a beveled surface. The bevel gears 163 are coupled to the first speed reducer 161 and the second speed reducer 162.

In this embodiment, the second speed reducer 162 is configured to further reduce the speed of the rotation provided from the bevel gears 163, and to provide the further-speed-reduced rotation. The second speed reducer 162 includes at least one of wave gearing reducer, an RV speed reducer and a Cyclo drive reducer (registered trademark). The RV speed reducer can be a two-stage speed reducer including a first stage of an eccentric differential type speed reducer, which includes pin gears as inner teeth and a trochoid gear as outer teeth, and a second stage of a spur gear speed reducer. In this embodiment, the second speed reducer 162 is wave gearing speed reducer. The wave gearing refers to a gear assembly including an elliptical gear and a circular gear and to provide differential rotation between them. Wave gear speed reducers are smaller and lighter than RV speed reducers and Cyclo speed reducers (registered trademark). One side of the second speed reducer 162 is coupled to the bevel gears 163 by screws 151 and is mounted to the first housing 141 by the screws 151. Another side of the second speed reducer 162 is mounted to the frame part 142*a* of the second housing 142 by screws 151.

In this embodiment, a reduction ratio r2 of the second speed reducer 162 shown in FIG. 14 is greater than a reduction ratio r1 of the first speed reducer 161. An available range of the reduction ratio r1 of the first speed reducer 161 is not smaller than 1 and not greater than 15. An available range of the reduction ratio r2 of the second speed reducer 162 is not smaller than 20 and not greater than 200. For example, a ratio r2/r1 between the ratio r2 of the second speed reducer 162 and the ratio r1 of the first speed reducer 161 can be approximately from 7 to 8. The six first speed reducers 161 shown in FIG. 14 have the same reduction ratio, but the speed reducers have different sizes. The second speed reducers 162 similarly have different sizes.

In this embodiment, a ratio r3 between the bevel gears 163 is smaller than the ratio r2 of the second speed reducer 162 and the ratio r1 of the first speed reducer 161. An available range of the reduction ratio r3 between the bevel gears 163 is not smaller than 2 and not greater than 5. For example, a ratio r1/r3 between the ratio r1 of the first speed reducer 161 and the ratio r3 between the bevel gears 163 can be approximately from 1.1 to 3. In FIG. 14, the JT2 axis, the JT4 axis, and the JT6 axis correspond to a bend axis. The gear parts on the JT2 axis, the JT4 axis and the JT6 axis correspond to the bevel gears 163. The bevel gears 163 installed on the JT2 axis, the JT4 axis and the JT6 axis have different sizes and different teeth numbers.

In this embodiment, as shown in FIG. 13, the servomotor SMB, the first speed reducer 161, the bevel gears 163 and the second speed reducer 162 are accommodated in the cylindrical first housing 141. The rotation axis AX2 of the servomotor SMB extends in the Zb direction, which is a longitudinal direction of the cylindrical first housing 141. In the first housing 141, the servomotor SMB, the first speed reducer 161, the bevel gears 163 and the second speed reducer 162 are arranged in this order. The servomotor SMB, the first speed reducer 161 and the bevel gears 163 are aligned in the Zb direction. The second speed reducer 162 is arranged on an Xb1 side of the bevel gears 163.

In this embodiment, the servomotor SMB, the first speed reducer 161 and the bevel gears 163 are arranged in the first housing 141 on one side with respect to a center line CL1 extending in the longitudinal direction of the cylindrical first housing 141 and passing through a center of the first housing 141. The second speed reducer 162 overlaps the center line CL1. The center line CL1 of the first housing 141 is a line that passes through the center in the Xb direction of the first housing 141, and extends in the Zb direction. The servomotor SMB, the first speed reducer 161 and the bevel gears 163 are arranged on the Xb2 side with respect to the center line CL1 in the first housing 141. The second speed reducer 162 straddles the center line CL1.

That is, in the joint 64B according to this embodiment, which is a bending joint, the rotation axis AX2 of the servomotor SMB agrees with the rotation axis AX2 of the first speed reducer 161; the rotation axis AX1 of the joint 64B agrees with the rotation axis AX1 of the second speed reducer 162; the rotation axis AX2 of the first speed reducer 161 and the rotation axis AX1 of the second speed reducer 162 are orthogonal to each other; and the bevel gears 163 transmit rotation of the first speed reducer into a direction orthogonal to the rotation axis AX2 of the first speed reducer 161.

(Detailed Structure of Twisting Joint Corresponding to Roll Axis)

Figure 15:
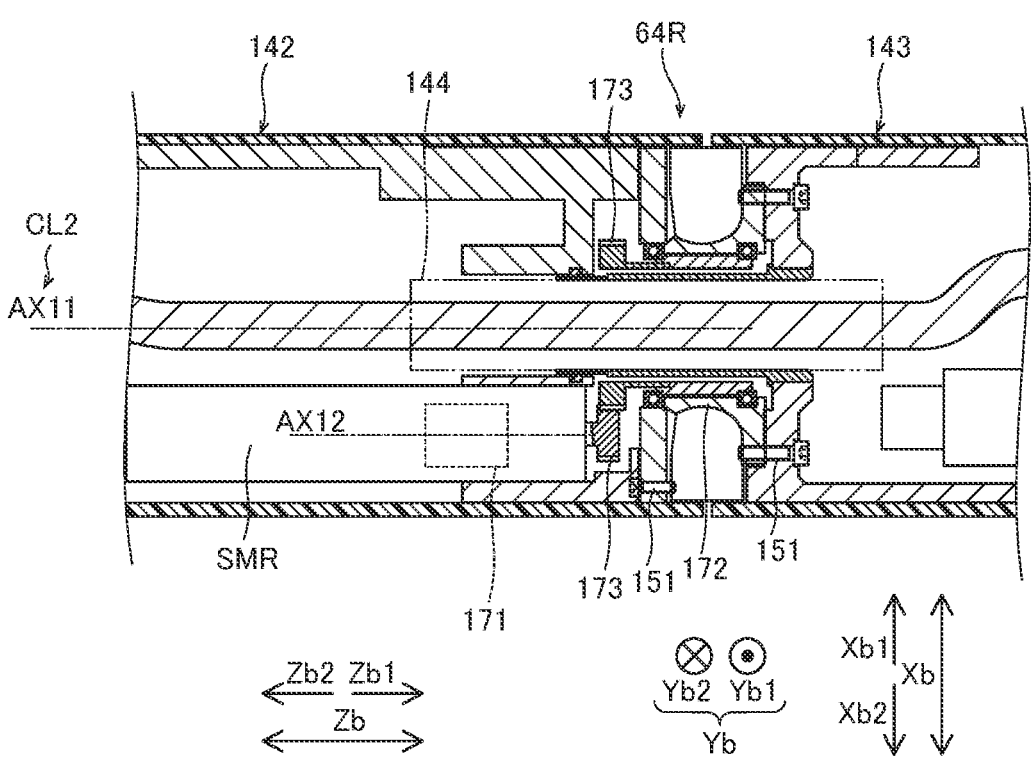
FIG. 15 is a cross-sectional diagram of a twisting joint according to the one embodiment as viewed in the Yb direction.

The detailed structure of the joint 64R as a twisting joint is now described. In this embodiment, as shown in FIG. 15, the joint 64R includes a servomotor SMR, a first speed reducer 171, helical gears 173 and a second speed reducer 172. The servomotor SMR is an example of a second electric motor. The first speed reducer 171 and the second speed reducer 172 are an example of a second-joint speed reducer. The helical gear is sometimes referred to as a skew gear or a helical tooth gear.

The servomotor SMR is arranged in the second housing 142. The servomotor SMB has a configuration similar to the servomotor SMR.

In this embodiment, the first speed reducer 171 is configured to reduce a speed of rotation of the servomotor SMR, and to provide the speed-reduced rotation. The servomotor SMR and the first speed reducer 171 are integrally formed. The first speed reducer 171 includes a planetary speed reducer. The first speed reducer 171 has a configuration similar to the first speed reducer 161.

In this embodiment, the helical gears 173 are configured to further reduce the speed of the rotation provided from the first speed reducer 171, and to provide the further-speed-reduced rotation. The helical gears 173 are configured to transmit the rotation of the servomotor SMR in a direction in parallel to the rotation axis AX12 of the servomotor SMR. The helical gears 173 are coupled to the first speed reducer 171 and the second speed reducer 172.

In this embodiment, the second speed reducer 172 is configured to further reduce the speed of the rotation provided from the helical gears 173, and to provide the further-speed-reduced rotation. One side of the second speed reducer 172 is coupled to the helical gears 173 and is mounted to the second housing 142 by screws 151. Another side of the second speed reducer 172 is mounted to the third housing 143 by screws 151. The second speed reducer 172 includes at least one of wave gearing reducer, an RV speed reducer and a Cyclo drive reducer (registered trademark).

In this embodiment, a reduction ratio r2 of the second speed reducer 172 shown in FIG. 14 is greater than a reduction ratio r1 of the first speed reducer 171. An available range of the reduction ratio r1 of the first speed reducer 171 is not smaller than 1 and not greater than 15. An available range of the reduction ratio r2 of the second speed reducer 172 is not smaller than 20 and not greater than 200. For example, r2/r1 between the ratio r2 of the second speed reducer 172 and the ratio r1 of the first speed reducer 171 can be approximately from 7 to 8. In FIG. 14, the JT1 axis, the JT3 axis, and the JT5 axis correspond to a roll axis. The gear parts on the JT1 axis, the JT3 axis and the JT5 axis correspond to the helical gears 173. The helical gears 173 installed on the JT1 axis, the JT3 axis and the JT5 axis have different sizes and different teeth numbers.

In this embodiment, reduction ratios of the helical gears 173 are smaller than the reduction ratio of the second speed reducers 172 and the reduction ratio of the first speed reducers 171. An available range of the reduction ratio r3 between the helical gears 173 is not smaller than 2 and not greater than 3. For example, a ratio r1/r3 between the ratio r1 of the first speed reducer 171 and the ratio r3 between the helical gears 173 can be approximately from 1.1 to 3. As shown in FIG. 14, the helical gears 173 have different sizes and different teeth numbers.

In this embodiment, as shown in FIG. 15, the servomotor SMR, the first speed reducer 171, the helical gears 173 and the second speed reducer 172 are accommodated in the cylindrical second housing 142. The rotation axis AX12 of the servomotor SMR extends in the Zb direction, which is a longitudinal direction of the cylindrical second housing 142. In the second housing 142, the servomotor SMR, the first speed reducer 171, the helical gears 173 and the second speed reducer 172 are arranged in this order. The servomotor SMB, the first speed reducer 171, the helical gears 173 and the second speed reducer 172 are aligned in the Zb direction.

In this embodiment, the servomotor SMR, the first speed reducer 171 and one of the helical gears 173 are arranged in the second housing 142 on one side with respect to the center line CL2 extending in the longitudinal direction of the cylindrical second housing 142 and passing through a center of the second housing 142. Another of the helical gears 173 and the second speed reducer 172 overlap the center line CL2 of the second housing 142. The center line CL2 of the second housing 142 is a line that passes through the center in the Xb direction and the Yb direction of the second housing 142, and extends in the Zb direction. The servomotor SMR, the first speed reducer 171, and the rotation axis AX12 of one of the helical gears 173 are arranged on the Xb2 side with respect to the center line CL2 in the second housing 142.

In this embodiment, as shown in FIG. 14, the plurality of first speed reducers 161 and the plurality of first speed reducers 161 in the plurality of joints 64 have a common speed reduction ratio r1. The plurality of second speed reducers 162 and the plurality of second speed reducers 172 in the plurality of joints 64 have a common speed reduction ratio r2. The bevel gear sets 163 and the helical gear sets 173 have different speed reduction ratios r3. As a result, the total reduction ratios r4 of the joints 64 are adjusted. In other words, speed reduction ratios r3a, r3b, r3c, r3d, r3e and r3f of the bevel gear sets 163 and the helical gear sets 173 are different from each other. Consequently, total gear ratios r4a, r4b, r4c, r4d, r4e and r4f of the joints 64 are adjusted.

That is, in this embodiment, the joint 64R is a twisting joint; the rotation axis AX12 of the servomotor SMR agrees with the rotation axis AX12 of the first speed reducer 171; the rotation axis AX11 of the joint 64R agrees with the rotation axis AX11 of the second speed reducer 172; the rotation axis AX12 of the first speed reducer 171 and the rotation axis AX11 of the second speed reducer 172 are parallel to each other; and the helical gears 173 transmit rotation of the first speed reducer into a direction parallel to the rotation axis AX12 of the first speed reducer 171.

(Wiring-Line Set)

As shown in FIG. 13, the wiring-line set 150 is accommodated in the joint 64B in this embodiment. The wiring-line set 150 is arranged in the robot arm 60 so that the wiring-line set 150 extends in the longitudinal direction of the robot arm 60, and passes through the rotation axis AX1 of the joint 64B and an AX1-Yb plane orthogonal to the longitudinal direction of the robot arm 60. Irrespective of a non-bent state of the robot arm 60 in which the first housing 141 and the second housing 142 extend in the Zb direction or a bent state of the robot arm 60 in which the first housing 141 and the second housing 142 intersect each other, the wiring-line set 150 is held while keeping passing through the rotation axis AX1 of the joint 64B and the AX1-Yb plane orthogonal to the longitudinal direction of the robot arm 60. The rotation axis AX1 of the joint 64B is also the rotation axis AX1 of the second speed reducer 162. The wiring-line set 150 includes power and signal lines. In a case in which a concept that an object is orthogonal to the rotation axis AX1 is stated, the concept includes that the object intersects the rotation axis AX1 at 90 degrees and that the object intersects the rotation axis AX1 at an angle around 90 degrees.

In this embodiment, the wiring-line set extends from an interior of the first housing 141 to an interior of the second housing 142. Specifically, the first housing 141 includes a first opening 141c. The second housing 142 includes a second opening 142c. The wiring-line set 150 passes through the first opening 141c and the second opening 142c. In the bent state of the robot arm 60 in which the first housing 141 and the second housing 142 intersect each other, the first opening 141c opens toward the Zb1 side. In the non-bent state of the robot arm 60 in which the first housing 141 and the second housing 142 extend in the Zb direction, the first opening 141c opens toward the Zb1 side. The first opening 141c is formed in the Yb direction. The second opening 142c opens toward the Zb2 side. The second opening 142c is formed in the Yb direction. The first opening 141c and the second opening 142c face each other.

In this embodiment, the first opening 141$c$ and the second opening 142$c$ are spaced away from each other in the longitudinal direction of the robot arm 60. In the non-bent state of the robot arm 60 in which the first housing 141 and the second housing 142 extend in the Zb direction, the first opening 141$c$ and the second opening 142$c$ are spaced away from each other in the Zb direction. Irrespective of the non-bent state of the robot arm 60 or the bent state of the robot arm 60, the first opening 141$c$ and the second opening 142$c$ are spaced away from each other. Accordingly, an end 141$d$ on the Zb1 side of the first housing 141 does not interfere with an end 142$d$ on the Zb2 side of the second housing 142.

Figure 16:
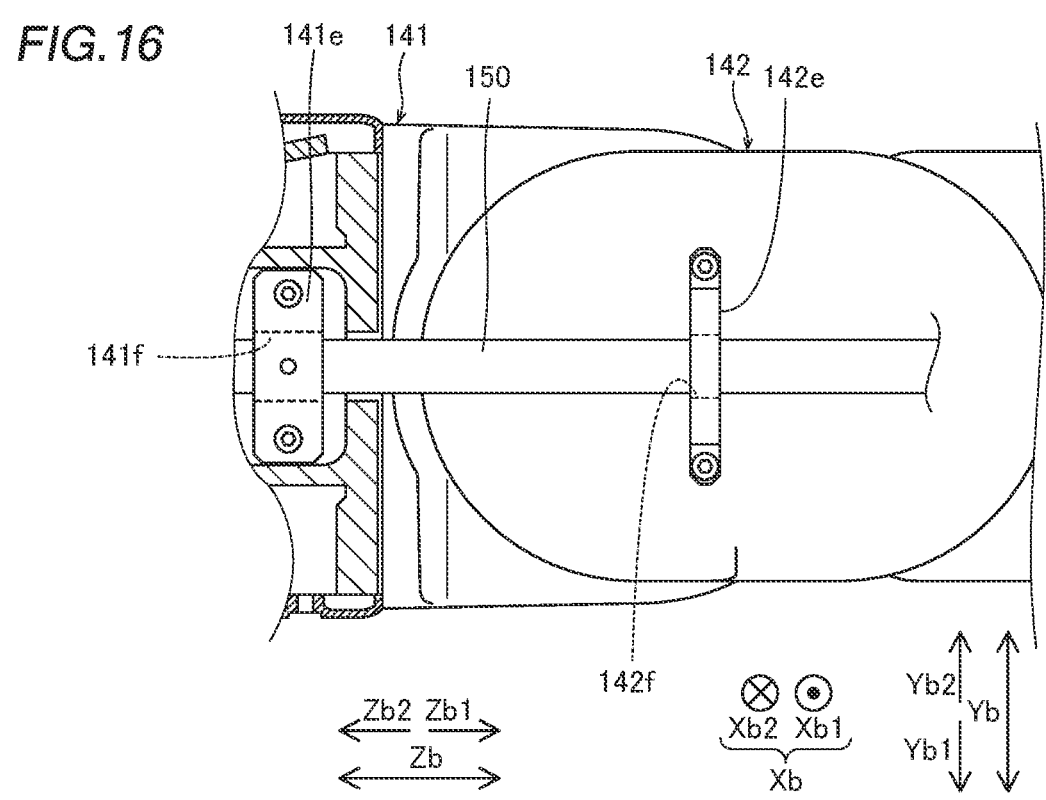
FIG. 16 is a cross-sectional diagram of a bending joint according to the one embodiment as viewed in an Xb direction.
Figure 17:
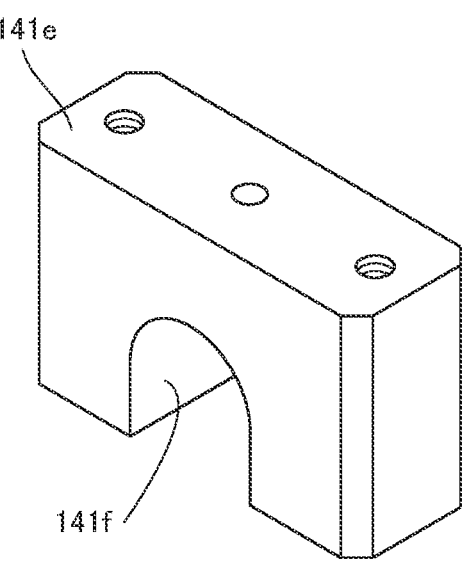
FIG. 17 is a perspective view of a first limiter according to the one embodiment.

In this embodiment, as shown in FIG. 16, the first housing 141 includes a first limiter 141$e$ configured to limit movement of the wiring-line set 150 extending from the second housing 142. As shown in FIG. 17, the first limiter 141$e$ has a U shape. The wiring-line set 150 is held in a cutout part 141$f$ formed between legs of the U-shaped first limiter 141$e$. The wiring-line set 150 is in contact with the cutout part 141$f$. This contact limits movement of the wiring-line set 150 in the Yb direction. The first limiter 141$e$ is mounted to the frame part 141$a$ of the first housing 141 by screws, etc. The first opening 141$c$ is formed of a gap between the frame part 141$a$ and the cover part 141$b$. The first limiter 141$e$ is arranged between the frame part 141$a$ and the cover part 141$b$.

Figure 18:
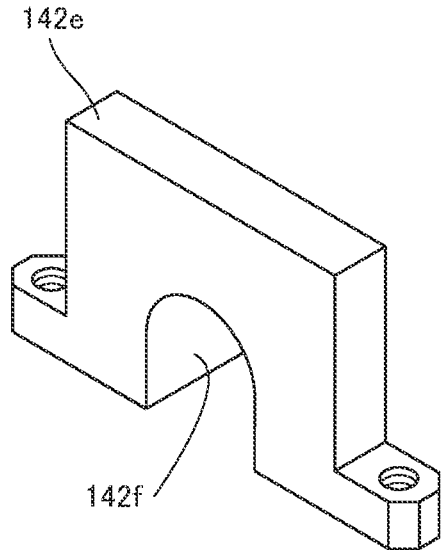
FIG. 18 is a perspective view of a second limiter according to the one embodiment.

In this embodiment, as shown in FIG. 16, the second housing 142 includes a second limiter 142$e$ configured to limit movement of the wiring-line set 150 extending from the first housing 141. As shown in FIG. 18, the second limiter 142$e$ has a U shape. The wiring-line set 150 is held in a cutout part 142$f$ formed between legs of the U-shaped second limiter 142$e$. The wiring-line set 150 is in contact with the cutout part 142$f$. This contact limits movement of the wiring-line set 150 in the Yb direction. As shown in FIG. 13, the second limiter 142$e$ is mounted to the frame part 142$a$ of the second housing 142 by screws, etc.

In this embodiment, the servomotor SMB is arranged in the first housing 141 on the Xb2 side with respect to the center line CL1 extending in the longitudinal direction of the first housing 141 and passing through the center of the first housing 141. The second speed reducer 162 overlaps the center line CL1, and the wiring-line set 150 is arranged on the Xb1 side with respect to the center line CL1. The first speed reducer 161 and the bevel gears 163 are arranged on the Xb2 side with respect to the center line CL1 of the first housing 141.

In this embodiment, as shown in FIG. 15, the second speed reducer 172 of the joint 64R is hollow. In the joint 64R, the wiring-line set 150 is held in the robot arm 60 so that the wiring-line set passes through an interior of the second speed reducer 172. The wiring-line set 150 passes through the first opening 141$c$ of the first housing 141 and the second opening 142$c$ of the second housing 142 so that the wiring-line set is accommodated in the second housing 142. The wiring-line set 150 passes through the second speed reducer 172, and then extends from the second housing 142 to the third housing 143. In other words, the wiring-line set 150 extends along the rotation axis AX11 of the joint 64R.

In this embodiment, a cylindrical wiring-line set protector 144 is provided. The wiring-line set protector 144 is arranged in the hollow second speed reducer 172, and receives the wiring-line set 150. The wiring-line set protector 144 is formed of an elastic material. The wiring-line set protector 144 is formed of a resin, for example. The wiring-line set protector 144 extends from the second housing 142 to the third housing 143. The wiring-line set protector 144 is not necessarily provided.

Advantages of the Embodiment

The wiring-line set 150 is arranged in the robot arm 60 so that the wiring-line set 150 extends in the longitudinal direction of the robot arm 60, and passes through the rotation axis AX1 of the joint 64B and an AX1-Yb plane orthogonal to the longitudinal direction of the robot arm 60. Consequently, because the wiring-line set 150 will not bulge in the rotation axis direction AX1 of the joint 64B, a width (thickness) in the rotation axis direction of the robot arm is not necessarily increased. Therefore, the robot arm 60 can be thinned.

The robot arm 60 includes a first housing 141 and a second housing 142 configured to relatively rotate with respect to each other by means of the joint 64B; and the wiring-line set 150 extends from an interior of the first housing 141 to an interior of the second housing 142. According to this configuration, because the wiring-line set 150, extends from an interior of the first housing 141 to an interior of the second housing 142, will not bulge in the rotation axis direction AX1, both the first housing 141 and the second housing 142 can be thinned.

The wiring-line set 150 passes through the first opening 141$c$ and the second opening 142$c$. According to this configuration, the wiring-line set 150 can easily extend from the interior of the first housing 141 to the interior of the second housing 142 through the first opening 141$c$ and the second opening 142$c$.

The first opening 141$c$ and the second opening 142$c$ are spaced away from each other in the longitudinal direction of the robot arm 60. According to this configuration, because the first opening 141$c$ and the second opening 142$c$ are spaced away from each other, the first housing 141 and the second housing 142 can be spaced away from each other. Consequently, interference between the first housing 141 and the second housing 142 can be prevented.

The first housing 141 includes a first limiter 141$e$ configured to limit movement of the wiring-line set 150 extending from the second housing 142. According to this configuration, movement of the wiring-line set 150 in the first housing 141 can be limited by the first limiter 141$e$.

The second housing 142 includes a second limiter 142$e$ configured to limit movement of the wiring-line set 150 extending from the first housing 141. According to this configuration, movement of the wiring-line set 150 in the second housing 142 can be limited by the second limiter 142$e$.

The wiring-line set 150 is arranged in the robot arm 60 so that the wiring-line set 150 extends in the longitudinal direction of the robot arm 60, and passes through the rotation axis AX1 of the second speed reducer 162 and through an AX1-Yb plane orthogonal to the longitudinal direction of the robot arm 60. According to this configuration, similar to a case that the wiring-line set 150 passes through an interior of a speed reducer, the wiring-line set 150 can be prevented from bulging in the rotation axis direction of the second speed reducer 162. Consequently, even in a case in which the second speed reducer 162 is arranged in the joint 64B, the robot arm 60 can be thinned.

The servomotor SMB is arranged in the first housing 141 on one side with respect to a center line CL1 extending in the longitudinal direction of the first housing 141 and passing through a center of the first housing 141; and the second speed reducer 162 overlaps the center line CL1, and the wiring-line set 150 is arranged on another side with respect to the center line CL1. According to this configuration, the servomotor SMB is arranged close to one side of the housing with respect to the center line CL1 of the housing, the wiring-line set 150 can be easily arranged on another side with respect to the center line CL1.

The wiring-line set 150 is arranged in the robot arm 60 so that the wiring-line set passes through an interior of the hollow second speed reducer 172. Here, because the joint 64R rotates about the longitudinal direction of the robot arm 60 as the rotation axis AX11, a pair of the second housings 142 and the third housing 143, which are coupled to each other by the joint 64R, are aligned on a straight line extending in the rotation axis AX11 direction. For this reason, although the wiring-line set 150 passes through an interior of the hollow second speed reducer 172 in the joint 64R, the wiring-line set 150 does not bulge.

The surgical robot 1 further includes a cylindrical wiring-line set protector 144 arranged in the hollow second speed reducer 172 to receive the wiring-line set 150. According to this configuration, damage to the wiring-line set 150 by contact between the second speed reducer 172 and the wiring-line set 150 can be prevented.

Modified Embodiment

Note that the embodiment disclosed this time must be considered as illustrative in all points and not restrictive. The scope of the present invention is not shown by the above description of the embodiments but by the scope of claims for patent, and all modifications or modified examples within the meaning and scope equivalent to the scope of claims for patent are further included.

That is, in this embodiment, the wiring-line set 150 passes through the first opening 141c of the first housing 141 and the second opening 142c of the second housing 142 has been shown in the aforementioned embodiment, the present invention is not limited to this. In the present disclosure, the first housing 141 may have a hole having a diameter similar to a diameter of the wiring-line set 150, and the second housing 142 may have a hole having a diameter similar to a diameter of the wiring-line set 150 so that the wiring-line set 150 passes through the hole of the first housing 141 and the hole of the second housing 142. According to this configuration, movement of the wiring-line set 150 can be limited by the hole of the first housing 141 and the hole of the second housing 142.

While the example in which the first opening 141c and the second opening 142c are spaced away from each other has been shown in the aforementioned embodiment, the present invention is not limited to this. In the present disclosure, the first opening 141c and the second opening 142c may be arranged adjacent to each other. In this arrangement, the first housing 141 and the second housing 142 are in contact with each other.

While the example in which movement of the wiring-line set 150 is limited by the first limiter 141e and the second limiter 142e, which have a U shape, has been shown in the aforementioned embodiment, the present invention is not limited to this. In the present disclosure, movement of the wiring-line set 150 may be limited by adhesive tape.

While the example in which the cylindrical wiring-line set protector 144 is arranged in an interior of the hollow second speed reducer 172 has been shown in the aforementioned embodiment, the present invention is not limited to this. In the present disclosure, the wiring-line set protector 144 may be omitted if interference between the wiring-line set 150 and the second speed reducer 172 unlikely to damage the wiring-line set 150.

While the example in which four robot arms 60 are provided has been shown in the aforementioned embodiment, the present disclosure is not limited to this. In the present disclosure, any number of robot arms 60 may be provided as long as at least one robot arms are provided.

While the example in which the arms 61 and the positioner 40 are constructed of a 7-axis multi-joint robot has been shown in the aforementioned embodiment, the present disclosure is not limited to this. For example, the arms 61 and the positioner 40 are constructed of a multi-joint robot having an axis configuration other than the 7-axis multi-joint robot. The multi-joint robot having an axis configuration other than the 7-axis multi-joint robot can be a 6-axis or 8-axis multi-joint robot, for example.

While the example in which the surgical robot 1 includes the medical cart 3, the positioner 40 and the arm base 50 has been shown in the aforementioned embodiment, the present disclosure is not limited to this. The medical cart 3, the positioner 40 and the arm base 50 are not necessarily provides, and the surgical robot 1 may include only the robot arms 60, for example.

Figure 19:
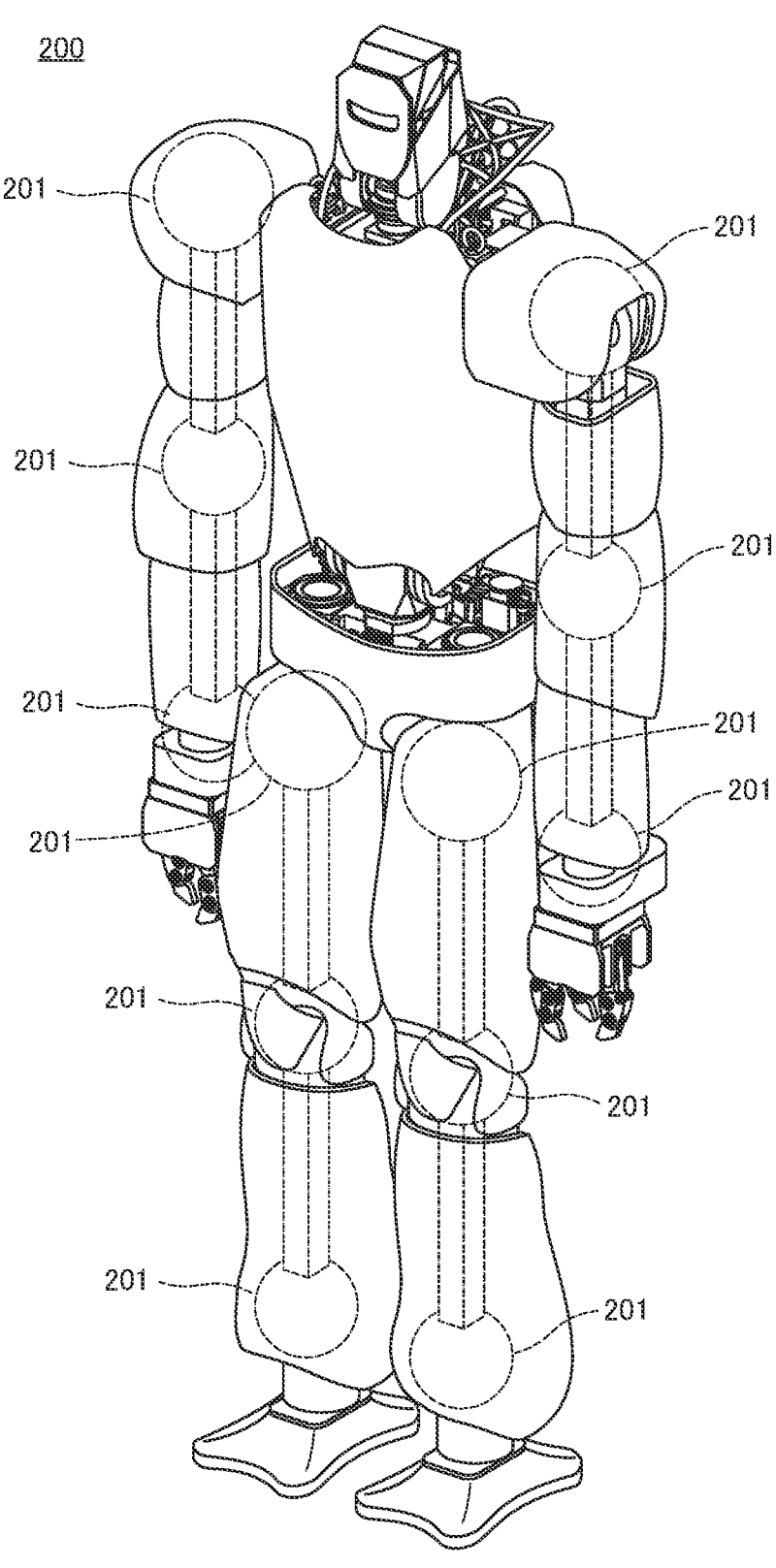
FIG. 19 is a diagram showing a humanoid robot according to a modified example.

While the example in which the present disclosure is applied to the surgical robot 1 has been shown in the aforementioned embodiment, the present disclosure is not limited to this. For example, the present disclosure may be applied to joints 201 of a humanoid robot 200 as shown in FIG. 19.

What is claimed is:

1. A surgical robot comprising a robot arm including a free end to which a surgical instrument is attached, and one or more joints; and
  a wiring-line set arranged in the robot arm, wherein
  the one or more joints include a first joint configured to rotate in a direction in which the robot arm is bent, and
  the wiring-line set is arranged in the robot arm so that the wiring-line set extends in a longitudinal direction of the robot arm, and passes through a rotation axis of the first joint and through a plane orthogonal to the longitudinal direction of the robot arm, wherein
  the first joint includes
  a first electric motor configured to rotate the first joint, and
  a first-joint speed reducer configured to transmit rotation of the first electric motor in a direction orthogonal to a rotation axis direction of the first electric motor, wherein
  the wiring-line set is arranged in the robot arm so that the wiring-line set extends in the longitudinal direction of the robot arm, and passes through a rotation axis of the first-joint speed reducer and through the plane orthogonal to the longitudinal direction of the robot arm.

2. The surgical robot according to claim 1, wherein
  the robot arm includes a first housing and a second housing configured to relatively rotate with respect to each other by means of the first joint; and
  the wiring-line set extends from an interior of the first housing to an interior of the second housing.

3. The surgical robot according to claim 2, wherein
  the first housing includes a first opening;
  the second housing includes a second opening; and
  the wiring-line set passes through the first opening and the second opening.

4. The surgical robot according to claim 3, wherein the first opening and the second opening are spaced away from each other in the longitudinal direction of the robot arm.

5. The surgical robot according to claim 4, wherein the first opening and the second opening are spaced away from each other in the longitudinal direction of the robot arm irrespective of a non-bent state in which the robot arm is not bent or a bent state in which the robot arm is bent.

6. The surgical robot according to claim 2, wherein the first housing includes a first limiter configured to limit movement of the wiring-line set extending from the second housing.

7. The surgical robot according to claim 6, wherein the first limiter has a U shape; and the wiring-line set is held in a cutout part formed between legs of the U-shaped first limiter.

8. The surgical robot according to claim 2, wherein the second housing includes a second limiter configured to limit movement of the wiring-line set extending from the first housing.

9. The surgical robot according to claim 8, wherein the second limiter has a U shape; and the wiring-line set is held in a cutout part formed between legs of the U-shaped second limiter.

10. The surgical robot according to claim 1, wherein
the robot arm further includes a cylindrical first housing that accommodates the first electric motor and the first-joint speed reducer;
the first electric motor is arranged in the first housing on one side with respect to a center line extending in the longitudinal direction of the first housing and passing through a center of the first housing;
the first speed reducer overlaps the center line; and
the wiring-line set is arranged on another side with respect to the center line.

11. The surgical robot according to claim 1, wherein
the one or more joints further include a second joint configured to rotate about the longitudinal direction of the robot arm as a rotation axis;
the second joint includes
a second electric motor configured to rotate the second joint, and
a hollow second-joint speed reducer configured to transmit rotation of the second electric motor in a direction parallel to a rotation axis direction of the second electric motor; and
the wiring-line set is arranged in the robot arm so that the wiring-line set passes through an interior of the hollow second-joint speed reducer.

12. The surgical robot according to claim 11 further comprising a cylindrical wiring-line set protector arranged in the hollow second-joint speed reducer to receive the wiring-line set.

13. The surgical robot according to claim 12, wherein the wiring-line set protector is formed of an elastic material.

14. The surgical robot according to claim 1, wherein the wiring-line set is arranged in the robot arm so that the wiring-line set passes through the rotation axis of the first joint and through the plane orthogonal to the longitudinal direction of the robot arm irrespective of a non-bent state in which the robot arm is not bent or a bent state in which the robot arm is bent.

15. A surgical robot comprising:
a robot arm including a free end to which a surgical instrument is attached, and first and second joints; and
a wiring-line set arranged in the robot arm, wherein
the first joint is configured to rotate in a direction in which the robot arm is bent, wherein the second joint is configured to rotate about a longitudinal direction of the robot arm as a rotation axis, and
the wiring-line set is arranged in the robot arm so that the wiring-line set extends in the longitudinal direction of the robot arm, and passes through a rotation axis of the first joint and through a plane orthogonal to the longitudinal direction of the robot arm, and extends along the rotation axis of the second joint, wherein
the first joint includes
a first electric motor configured to rotate the first joint, and
a first-joint speed reducer configured to transmit rotation of the first electric motor in a direction orthogonal to a rotation axis direction of the first electric motor; and
the wiring-line set is arranged in the robot arm so that the wiring-line set extends in the longitudinal direction of the robot arm, and passes through a rotation axis of the first-joint speed reducer and through the plane orthogonal to the longitudinal direction of the robot arm.

16. The surgical robot according to claim 15 wherein,
the robot arm further includes a cylindrical first housing that accommodates the first electric motor and the first-joint speed reducer;
the first electric motor is arranged in the first housing on one side with respect to a center line extending in the longitudinal direction of the first housing and passing through a center of the first housing;
the first-joint speed reducer overlaps the center line; and
the wiring-line set is arranged on another side with respect to the center line.

17. The surgical robot according to claim 15, wherein
the second joint includes
a second electric motor configured to rotate the second joint, and
a hollow second-joint speed reducer configured to transmit rotation of the second electric motor in a direction parallel to a rotation axis direction of the second electric motor; and
the wiring-line set is arranged in the robot arm so that the wiring-line set passes through an interior of the hollow second-joint speed reducer.

18. A robotic surgical system comprising:
a patient-side device including a robot arm that includes a free and to which a surgical instrument is attached, and one or more joints;
an operator-side device including an operation unit configured to accept an instruction from an operator; and
a wiring-line set arranged in the robot arm, wherein
the one or more joints include a first joint configured to rotate in a direction in which the robot arm is bent, and
the wiring-line set is arranged in the robot arm so that the wiring-line set extends in a longitudinal direction of the robot arm, and passes through a rotation axis of the first joint and through a plane orthogonal to the longitudinal direction of the robot arm, wherein
the first joint includes
a first electric motor configured to rotate the first joint, and
a first-joint speed reducer configured to transmit rotation of the first electric motor in a direction orthogonal to a rotation axis direction of the first electric motor, wherein
the wiring-line set is arranged in the robot arm so that the wiring-line set extends in the longitudinal direction of the robot arm, and passes through a rotation axis of the first-joint speed reducer and through the plane orthogonal to the longitudinal direction of the robot arm.

* * * * *